United States Patent
Jacquot

(10) Patent No.: US 6,881,869 B1
(45) Date of Patent: Apr. 19, 2005

(54) METHOD FOR PREPARING SUBSTITUTED MIXED ALKYNYL ETHERS

(75) Inventor: Roland Jacquot, Francheville (FR)

(73) Assignee: Rhodia Chimie, Boulogne Billancourt (FR)

( * ) Notice: Subject to any disclaimer, the term of this patent is extended or adjusted under 35 U.S.C. 154(b) by 103 days.

(21) Appl. No.: 10/088,455

(22) PCT Filed: Sep. 29, 2000

(86) PCT No.: PCT/FR00/02704

§ 371 (c)(1),
(2), (4) Date: Mar. 13, 2002

(87) PCT Pub. No.: WO01/23338

PCT Pub. Date: Apr. 5, 2001

(30) Foreign Application Priority Data

Sep. 29, 1999 (FR) .............................. 99 12146

(51) Int. Cl.⁷ .............................................. C07C 41/00
(52) U.S. Cl. ...................................................... 568/626
(58) Field of Search ........................................ 568/626

(56) References Cited

FOREIGN PATENT DOCUMENTS

| FR | 2522648 | 9/1983 | ......... C07C/43/215 |
| WO | WO 97/19040 | 5/1997 | |
| WO | WO 99/02475 | 1/1999 | ........... C07C/41/09 |

OTHER PUBLICATIONS

Makabe et al, Heterocycles, vol. 43 No. 10, 1996.*
Hatayeyamna et al, Tetrahedron Letters, vol. 50, No. 47, pp13369–13373.*
Kobayashi et al, JACS, 1998, vol. 120, pp. 908–919.*
Chong et al, Tetrahedron Letters, vol. 27, No. 45, pp. 5445–5448.*
Kobayashi et al, JACS, 1998, vol. 120, pp. 908–919.*
Chong et al, Tetrahedron Letters, vol. 27, No. 45, pp. 5445–5448.*
J.M. Chong: "Alkylation of stabilized acetylides in DMSO. Preparation of alpha, beta– acetylenic alcohols and acetals" Tetrahedron Letters, vol. 27, No. 45, 1986, pp. 5445–5448, XP002138832. Oxford GB, p. 5445—p. 5446.
International Search Report.

* cited by examiner

Primary Examiner—Rita Desai
Assistant Examiner—Hector M. Reyes

(57) ABSTRACT

The present invention relates to a process for preparing mixed substituted alkynyl ethers. More particularly, the invention concerns the preparation of mixed ethers derived from a benzyl type alcohol and a substituted alkynyl alcohol. The process of the invention for preparing a benzyl/substituted alkynyl type mixed ether is prepared from a benzyl/alkynyl type mixed ether with a hydrogen atom on the triple bond is characterized in that it consists of reacting a mixed ether derived from a benzyl type alcohol and an alkynyl alcohol with a hydrogen atom on the triple bond with an alkylation agent, in the presence of an anionisation agent.

24 Claims, No Drawings

METHOD FOR PREPARING SUBSTITUTED MIXED ALKYNYL ETHERS

This application is an application under 35 U.S.C. Section 371 of International Application Number PCT/FR00/02704 filed on Sep. 29, 2000.

The present invention relates to a process for preparing mixed substituted alkynyl ethers. More particularly, the invention relates to the preparation of mixed ethers derived from a benzyl type alcohol and a substituted alkynyl alcohol.

International patent application PCT/FR98/01472 describes a process for etherifying a benzyl type alcohol that consists of reacting said alcohol with a further alcohol, in the presence of a catalyst, said process being characterized in that the etherification reaction is carried out in the presence of an effective quantity of a zeolite.

The benzyl type alcohol employed has the following general formula:

(F1)

in which:

A represents the residue of a cycle forming all or part of an aromatic, monocyclic or polycyclic, carbocyclic or heterocyclic system;

R represents one or more substituents that may be identical or different;

$R_1$ and $R_2$, which may be identical or different, represent a hydrogen atom, a functional group or a hydrocarbon group containing 1 to 24 carbon atoms;

n is a number equal to 5 or less.

The term "benzyl type alcohol" as used in the description of the present invention means not only an aromatic carbocycle but also an aromatic heterocycle wherein one hydrogen atom directly bonded to the aromatic ring is replaced by a group:

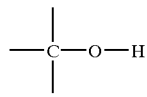

and the term "aromatic" means the conventional notion of aromaticity as defined in the literature, in particular by Jerry MARCH, "Advanced Organic Chemistry", $4^{th}$ edition, John Wiley and Sons, 1992, pp. 40 ff.

The alcohol caused to react has the following formula:

$R_5$—OH (F2)

in which $R_5$ represents a hydrocarbon group containing 1 to 24 carbon atoms, which can be a linear or branched, saturated or unsaturated, acyclic aliphatic group; a saturated, unsaturated or aromatic cycloaliphatic group; or a linear or branched, saturated or unsaturated aliphatic group, carrying a cyclic substituent.

The ether of the benzyl type alcohol with formula (F1) and the alcohol with formula (F2) obtained can be symbolised by formula (F3):

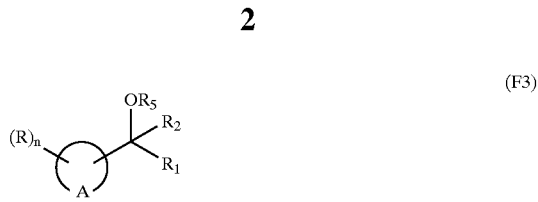

(F3)

in which:

A, n, R, $R_1$, $R_2$ and $R_5$ have the meanings given above.

Alcohols with formula (F2) that can be used include unsaturated alcohols such as substituted alkynyl alcohols, in particular 2-butyn-1-ol represented by the formula

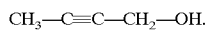

$CH_3$—C≡C—$CH_2$—OH.

The disadvantage of using such a substituted alkynyl alcohol resides in its very high cost compared with the propargylic alcohol with formula H—C≡C—$CH_2$—OH.

The aim of the present invention is to provide a cheap process for preparing an ether derived from a benzyl type alcohol and a substituted alkynyl alcohol, i.e., in which the hydrogen atom of the alkyne function has been substituted by a hydrocarbon group.

It has now been discovered, and this constitutes the subject matter of the present invention, a process for preparing a mixed ether of the benzyl/substituted alkynyl type from a mixed ether of the benzyl/alkynyl type with a hydrogen atom on the triple bond, characterized in that it consists of reacting a mixed ether derived from a benzyl type alcohol and an alkynyl alcohol carrying a hydrogen atom on the triple bond with an alkylation agent, in the presence of an anionisation agent.

In accordance with the process of the invention, the starting substance is a true alkynyl mixed ether, i.e., the alkyne function carries a hydrogen atom.

More precisely, we start from an ether derived from a benzyl type alcohol and an alkynyl alcohol, with general formula (I):

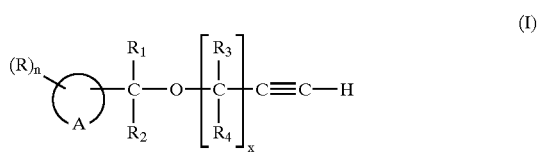

(I)

in which:

A represents the residue of a cycle forming all or part of an aromatic, monocyclic or polycyclic, carbocyclic or heterocyclic system comprising at least one group

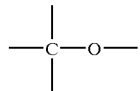

R represents one or more substituents which may be identical or different;

$R_1$ and $R_2$, which may be identical or different, represent a hydrogen atom, a functional group or a hydrocarbon group containing 1 to 24 carbon atoms, which can be a linear or branched, saturated or unsaturated acyclic aliphatic group; a saturated, unsaturated or aromatic, monocyclic or polycyclic cycloaliphatic group; or a linear or branched, saturated or unsaturated aliphatic group carrying a cyclic substituent;

$R_3$ and R4, which may be identical or different, represent a hydrogen atom or a hydrocarbon group containing 1 to 12 carbon atoms;

n is a number equal to 5 or less;

x is a number from 1 to 10, preferably 1 to 5.

The mixed alkynyl ether involved in the process of the invention satisfies formula (I) in which $R_1$ and $R_2$ represent a linear or branched, saturated or unsaturated, acyclic aliphatic group.

More preferably, $R_1$ and $R_2$ represent a linear or branched alkyl group containing 1 to 12 carbon atoms, preferably 1 to 6 carbon atoms; the hydrocarbon chain can optionally be interrupted by a heteroatom (for example oxygen), by a functional group (for example —CO—) and/or may carry a substituent (for example a halogen).

The linear or branched, saturated or unsaturated, acyclic aliphatic group can optionally carry a cyclic substituent. The term "cycle" preferably means a saturated, unsaturated or aromatic, carbocylic or heterocyclic cycle, preferably cycloaliphatic or aromatic, in particular cycloaliphatic comprising 6 carbon atoms in the cycle, or a benzene ring. The aliphatic acyclic group can be connected to the cycle by a covalent bond, a heteroatom or a functional group; examples are given below.

The cycle can optionally be substituted; possible examples of cyclic substituents are substituents such as R, the meaning of which has been defined above.

$R_1$ and $R_2$ can also represent a saturated carbocylic group or a carbocyclic group comprising 1 or 2 unsaturated bonds in the cycle, generally containing 3 to 8 carbon atoms, preferably 6 carbon atoms in the cycle; said cycle can be substituted by substituents such as R.

$R_1$ and $R_2$ can also represent an aromatic carbocyclic group, preferably monocyclic, generally containing at least 4 carbon atoms, preferably 6 carbon atoms in the cycle; said cycle may be substituted by substituents such as R.

One of groups $R_1$ and $R_2$ can represent a group $CF_3$.

The invention is of particular application to mixed alkynyl ethers with formula (I) in which A is the residue of a cyclic compound preferably containing at least 4 carbon atoms in the cycle, more preferably 5 or 6, optionally substituted, and representing at least one of the following cycles:

an aromatic, monocyclic or polycyclic carbocycle;

an aromatic, monocyclic or polycyclic heterocycle comprising at least one of heteroatoms O, N or S.

Without in any way limiting the scope of the invention, optionally substituted residue A can represent the residue:

of an aromatic carbocyclic monocyclic compound such as benzene or toluene;

of an aromatic condensed polycyclic compound such as naphthalene;

or an aromatic, heterocyclic, monocyclic compound such as pyridine, furan or thiophene.

In the process of the invention, a mixed alkynyl ether with formula (I) is preferably used wherein A represents a benzene or naphthalene nucleus.

Residue A of the mixed alkynyl ether with formula (I) can carry one or more substituents provided that they do not react with the anionisation agent.

The number of substituents present on the cycle depends on the carbon condensation of the cycle and on the presence or otherwise of unsaturated bonds on the cycle.

The maximum number of substituents that are capable of being carried by a cycle can readily be determined by the skilled person.

Examples of substituents are given below, but this list is not limiting in any way. The following can be cited in particular:

linear or branched alkyl groups, preferably containing 1 to 6 carbon atoms, more preferably 1 to 4 carbon atoms;

linear or branched alkenyl groups, preferably containing 2 to 6 carbon atoms, more preferably 2 to 4 carbon atoms;

linear or branched halogenoalkyl groups, preferably containing 1 to 6 carbon atoms, more preferably 1 to 4 carbon atoms;

cycloalkyl groups containing 3 to 6 carbon atoms, preferably the cyclohexyl group;

the phenyl group;

alkoxy $R_5$—O— or thioether $R_5$—S— groups, in which $R_5$ represents a linear or branched alkyl group containing 1 to 6 carbon atoms, more preferably 1 to 4 carbon atoms or a phenyl group;

—$N(R_6)_2$ groups, in which $R_6$ groups, which may be identical or different, represent a hydrogen atom, a linear or branched alkyl group containing 1 to 6 carbon atoms, preferably 1 to 4 carbon atoms, or a phenyl group;

the group $CF_3$.

When n is 2 or more, two groups R and the 2 successive atoms on the aromatic cycle can be bonded together via an alkylene, alkenylene or alkenylidene group containing 2 to 4 carbon atoms to form a saturated, unsaturated or aromatic heterocycle containing 5 to 7 carbon atoms. One or more carbon atoms may be replaced by a further heteroatom, preferably oxygen. Groups R can represent a methylenedioxy or ethylenedioxy group.

Preferred substituents are selected from electron-donating groups. The term "electron-donating group" means a group as defined by H. C. BROWN in the work by Jerry MARCH, "Advanced Organic Chemistry", Chapter 9, pages 243 and 244 (1985).

Regarding the meanings of $R_3$ and $R_4$ in formula (I), they more particularly represent a hydrogen atom or a linear or branched alkyl group containing 1 to 12 carbon atoms, preferably 1 to 4.

Preferred groups that can be mentioned for $R_3$ and $R_4$ are a hydrogen atom, a methyl, ethyl, propyl or isopropyl group.

Preferably, $R_3$ and $R_4$ represent a hydrogen atom.

In formula (I), x is a number equal to 1, 2 or 3.

More particularly, the process of the invention is applicable to mixed alkynyl ethers with formula (Ia):

$$(R)_n \underset{}{\underset{}{\bigcirc}} \overset{R_1}{\underset{R_2}{-C-}} O \left[ \overset{R_3}{\underset{R_4}{-C-}} \right]_x C \equiv C - H \qquad (Ia)$$

in which:

a is a number equal to 4 or less, preferably 1 or 2;

x is a number equal to 1, 2 or 3;

group or groups R are electron-donating groups, preferably an alkyl or alkoxy group containing 1 to 4 carbon atoms, or methylenedioxy or ethylenedioxy;

groups $R_1$ or $R_2$, which may be identical or different, represent:

a hydrogen atom;

a linear or branched alkyl group containing 1 to 6 carbon atoms, preferably 1 to 4 carbon atoms, such as methyl, ethyl, propyl, isopropyl, butyl, isobutyl, sec-butyl, tert-butyl;

a cycloalkyl group containing 3 to 8 carbon atoms, preferably a cyclopentyl or cyclohexyl group;
a phenyl group;
a phenylalkyl group containing 7 to 12 carbon atoms, preferably a benzyl group;
a $CF_3$ group;
groups $R_3$ and $R_4$, which may be identical or different, represent a hydrogen atom or a linear or branched alkyl group containing 1 to 4 carbon atoms.

Preferred compounds satisfy formula (Ia) in which:
n is a number equal to 1 or 2;
x is a number equal to 1, 2 or 3;
groups R, which may be identical or different, represent an alkyl or alkoxy group containing 1 to 4 carbon atoms, or methylenedioxy or ethylenedioxy;
groups $R_1$ and $R_2$, which may be identical or different, represent:
a hydrogen atom;
a linear or branched alkyl group containing 1 to 6 carbon atoms, preferably 1 to 4 carbon atoms, such as methyl, ethyl, propyl, isopropyl, butyl, isobutyl, sec-butyl, tert-butyl;
groups $R_3$ and $R_4$ which may be identical or different, represent a hydrogen atom or a linear or branched alkyl group containing 1 to 4 carbon atoms. More particular compounds with formula (Ia) are mixed alkynyl ethers with formula (Ib):

$$(R)_n\text{-Ar-}\underset{H}{\overset{R_1}{\underset{|}{\overset{|}{C}}}}-O-\left[\underset{R_4}{\overset{R_3}{\underset{|}{\overset{|}{C}}}}\right]_x-C\equiv C-H \quad (Ib)$$

in which:
n is equal to 1 or 2;
group or groups R represent an alkyl or alkoxy group containing 1 to 4 carbon atoms, or methylenedioxy;
group $R_1$ represents a hydrogen atom or a linear or branched alkyl group containing 1 to 4 carbon atoms.

Compounds with formula (1) can be prepared as described in PCTAFR/98/01472 using a process that consists of reacting, in the presence of a zeolite:
a benzyl type alcohol with formula:

$$(R)_n\text{-A-}\underset{R_1}{\overset{OH}{\underset{|}{\overset{|}{C}}}}-R_2 \quad (II)$$

in which formula, R, $R_1$, $R_2$, A and n have the meaning given above;
and an unsaturated alcohol with formula:

$$HO-\left[\underset{R_4}{\overset{R_3}{\underset{|}{\overset{|}{C}}}}\right]_x-C\equiv CH \quad (III)$$

in which formula $R_3$, $R_4$ and x have the meanings given above.

Compounds (H) and (II) are reacted in the presence of a zeolite.
Preferably, a zeolite is used such as:
mordenite with a Si/Al mole ratio of 5 to 150, preferably 10 to 100, more preferably 10to 25;
β zeolites with a Si/Al mole ratio of more than 8, preferably in the range 10 to 100, more preferably in the range 12 to 50;
Y zeolites with a Si/Al mole ratio in the range 2 to 50, preferably in the range 2 to 15.

The benzyl type alcohol with formula (II) can be reacted with the unsaturated alcohol with formula (III) in the presence or absence of an organic solvent, and one of the reactants can be used as the reaction solvent.

Non limiting examples of solvents that are suitable for use in the present invention that can be cited are aliphatic, cycloaliphatic or aromatic ether-oxides, more particularly diethyl oxide, dipropyl oxide, diisopropyl oxide, dibutyl oxide, methytertiobutylether, dipentyl oxide, diisopentyl oxide, phenyl oxide, benzyl oxide; dioxane, and tetrahydrofliran (THF).

When the process is carried out in batches, the catalyst can represent 2% to 50%, preferably 5% to 20% by weight with respect to the lowest quantity of reactant. However, if the process is carried out continuously, for example by reacting a mixture of benzyl type alcohol and unsaturated alcohol on a fixed catalyst bed, these catalyst/benzyl alcohol ratios have no significance and at a given time, there may be an excess weight of catalyst with respect to the starting benzyl alcohol.

The quantity of unsaturated alcohol with formula (III) expressed in moles of unsaturated alcohol per mole or benzyl type alcohol with formula (II) can also vary widely. The mole ratio of unsaturated alcohol with formula (III)/ benzyl alcohol with formula (I) can be between 1 and 30. The upper limit is not critical but there is no advantage in exceeding it, for economic reasons.

The temperature of the etherification reaction can vary widely. It is advantageously in the range 50° C. to 200° C., more preferably in the range 50° C. to 100° C.

Generally, the reaction is carried out at atmospheric pressure, but higher pressures of 1 to 50 bars, preferably 1 to 25 bars, may also be suitable. Autogenous pressure conditions are used when the reaction temperature is higher than the boiling point of the reactants and/or products.

Preferably, the reaction is carried out in a controlled inert gas atmosphere, for example nitrogen or a rare gas such as argon.

The reaction period can vary widely. It is usually in the range 15 minutes to 10 hours, preferably in the range 30 minutes to 5 hours.

From a practical viewpoint, the process can be carried out continuously or in batches.

In a first variation, the catalyst, unsaturated alcohol with formula (III), and optional organic solvent can be charged then the benzyl type alcohol can be introduced. In a preferred implementation of the invention, the benzyl type alcohol is introduced progressively, either continuously or in aliquots, then the reaction mixture is heated to the desired temperature.

In a further variation of the invention, the reaction is carried out continuously in a tube reactor comprising the solid catalyst disposed in a fixed bed.

The benzyl type alcohol and the unsaturated alcohol are preferably introduced separately.

They can also be introduced into a solvent as mentioned above.

The residence time for the flow of material on the catalytic bed can be, for example, between 15 min and 10 hours, preferably in the range 30 min to 5 hours.

At the end of the reaction, a liquid phase is recovered comprising the etherified benzyl type alcohol with formula (I) which can be recovered conventionally.

In the process of the invention, C-alkylation of the compound with formula (I) obtained initially is carried out with the help of an alkylation agent. A first class of alkylation agents that can be used in the process of the invention is constituted by dialkylsulphates.

To this end, dialkylsulphates with the following formula are used:

$$R_7-O-SO_2-O-R_7 \quad \text{(IVa)}$$

in which $R_7$ represents a linear or branched alkyl group containing 1 to 6 carbon atoms.

Dimethylsulphate is preferred from the above alkylation agents.

A further suitable class is constituted by halide type compounds, in particular those represented by the following formula:

$$R_8-X \quad \text{(IVb)}$$

in which:

R represents a hydrocarbon group containing 1 to 20 carbon atoms, which can be a linear or branched, saturated or unsaturated, acyclic aliphatic group; a saturated, unsaturated or aromatic, monocyclic or polycyclic cycloaliphatic group; or a linear or branched, saturated or unsaturated aliphatic group carrying a cyclic substituent;

X represents a bromine, chlorine or iodine atom.

The term "cycle" preferably means a saturated, unsaturated or aromatic carbocyclic or heterocyclic cycle, preferably cycloaliphatic or aromatic, in particular cycloaliphatic, containing 6 carbon atoms in the cycle, or a benzene ring.

Particularly suitable compounds with formula (IVb) are those in which $R_8$ represents a linear or branched $C_1$ to $C_{10}$ alkyl group, a $C_3$ to $C_{10}$ cycloalkyl group, a $C_6$ to $C_{12}$ aryl group or a $C_7$ to $C_{15}$ arylalkyl group, such as a benzyl group.

More preferably, it is a $C_1$ to $C_{10}$ alkyl group; the alkyl chain may be interrupted by one or more oxygen atoms.

Preferred halides with formula (IVb) are those with formula (IVb) in which X is a chlorine or iodine atom and $R_8$ is a linear or branched alkyl group containing 1 to 4 carbon atoms.

More particularly, the following are employed: methyl iodide, methyl chloride, chloroethane, methyl bromide and bromoethane.

The quantity of alkylation agent used is equal to or greater than the stoichiometric quantity necessary to alkylate the hydrogen atom on the alkyne function.

Generally, the alkylation agent is employed in a quantity such that the ratio between the number of moles of alkylation agent and the number of hydrogen atoms replaced by an alkyl group $R_9$ ($R_9$ representing $R_7$ or $R_8$) is in the range 1 to 2, preferably in the range 1.1 to 1.3.

In accordance with the process of the invention, the mixed alkynyl ether with formula (I) and the alcylation agent are reacted in the presence of an agent for anionising the alkyne function to transform it into a C≡C function.

Examples of reactants that can be cited in particular are amide type bases, metallic alcoholates and alkali metals.

An organic amide type base can be used, for example lithium diisopropylatnide, lithium hexamethyldisilazane prepared or used in situ by the action of a strong lithiated base on the corresponding amine but preferably, a mineral salt is used, preferably an alkali metal amide, more particularly sodium or potassium amide.

For economic reasons, sodium amide is used.

It is also possible to use an alkali metal alcoholate, preferably a sodium or potassium alcoholate, more preferably sodium or potassium methylate, ethylate or tert-butylate.

It is also possible to use an alkali metal, preferably sodium or potassium.

The quantity of anionisation agent is at least equal to the stoichiometric quantity required, but it is generally employed in an excess of up to 20%.

The reaction is carried out in an organic solvent that is inert as regards the anionisation agent. Aliphatic or aromatic hydrocarbons can in particular be mentioned.

Examples of aliphatic hydrocarbons that can in particular be cited are paraffins such as hexane, heptane, octane, nonane, decane, undecane, dodecane, tetradecane or cyclohexane, and aromatic hydrocarbons, more particularly aromatic hydrocarbons such as benzene, toluene, xylenes, cumene and petroleum cuts constituted by a mixture of alkylbenzenes, particularly Solvesso® type cuts.

Toluene is preferred from the above list.

The quantity of organic solvent used can vary widely. It is such that the concentration by weight of the compound is advantageously in the range 5% to 50%, preferably in the range 20% to 30%.

The temperature at which the process of the invention is carried out is generally between 20° C. and the reflux temperature of the reaction mixture, preferably between 50° C. and 80° C.

The reaction pressure is selected by the skilled person as a function of the alkylation agent. It can be in the range $10^{-2}$ to 50 bars, preferably atmospheric pressure.

Preferably, the process of the invention is carried out in an inert gas atmosphere. A rare gas atmosphere can be employed, preferably argon, but nitrogen is cheaper.

From a practical viewpoint, the process of the invention is easy to carry out as no specific apparatus is required.

Practically, the process of the invention can be carried out as follows.

The various constituents of the reaction mixture are charged into the selected apparatus. The order of introduction is not critical. Preferably, the compound with formula (I) and the anionisation agent are brought into contact. The reaction medium is heated to the desired temperature, then the alkylation agent is added.

The desired product is recovered conventionally.

As an example, water can be added to re-dissolve the salts in an aqueous phase and an extraction solvent can be added, for example toluene.

The product obtained has formula (IV):

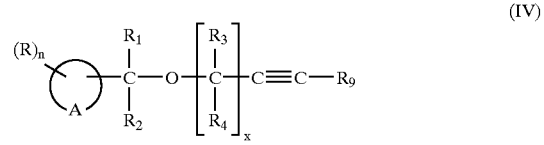

in which formula, the different symbols have the meanings given above.

Non limiting illustrative examples will now be given.

The terms TT and RR mean:

Degree of converstaion(TT) =

$$\frac{\text{number of moles of reactant transformed}}{\text{Number of moles of reactant introduced}}(\%)$$

$$\text{Yield}(RR) = \frac{\text{number of moles of alkynyl ether formed}}{\text{Number of moles of benzyl alcohol introduced}}(\%)$$

EXAMPLE 1

Preparation of [1-prop-1-ynyloxy)ethyl]-3,4 dimetboxybenzene 260 g of 1-[3,4dimethoxyphenyl]-ethan-1-ol and 400 g of propargyl alcohol were introduced into a 1000 ml three-necked reactor.

It was stirred, and 40 g of HY zeolite with a Si/Al ratio of 2.7 was added.

It was slowly heated to 85° C.

It was maintained under these conditions for 2 hours.

It was cooled to 50° C and the catalyst was filtered off.

The excess propargyl alcohol was distilled off and recycled under reduced pressure.

Gas chromatographic analysis produced the following results:

TT: 100%; RR: 98%.

Preparation of [1-but-1-ynyloxy)ethyl]-3,4 dimetboxybenzene 100 ml of toluene was introduced into a 1000 ml reactor. It was stirred and the reactor was placed under a stream of nitrogen.

47 g of sodium amide was introduced.

With continuous stirring, a solution composed of 100 ml of toluene and 220 g of [1-prop-1-ynyloxy)ethyl]-3,4 dimethoxybenzene was added over 10 minutes.

It was heated to 80° C. and kept under these conditions for 2 hours.

The reaction mixture was cooled to 20° C. and 126 g of methyl sulphate was added over 15 min.

It was stirred for 1 hour at ambient temperature.

100 ml of water was added at ambient temperature.

It was decanted and the organic layer was washed with 100 ml of water.

It was concentrated and gas chromatographic analysis produced the following:

TT: 100%; RR: 98%.

EXAMPLE 2

Preparation of [1-but-1-ynyloxy)ethyl]-3,4 dimethoxybenzene 100 ml of toluene and 30 g of sodium were introduced into a 1000 ml reactor. It was stirred and the reactor was placed in a stream of nitrogen. It was heated to 120° C. to melt the sodium and rapidly cooled to produce a dispersion of sodium. The preparation was continued as described in Example 1.

Gas chromatographic determination produced the following:

TT: 82%; RR 56%.

What is claimed is:

1. A process for preparing a substituted mixed alkynyl ether from a starting mixed alkynyl ether comprising a hydrogen atom on a triple bond, said process comprising the steps of:

a) reacting said starting mixed ether of the following formula (I):

$$(R)_n - A - \underset{R_2}{\overset{R_1}{\underset{|}{\overset{|}{C}}}} - O - \left[\underset{R_4}{\overset{R_3}{\underset{|}{\overset{|}{C}}}}\right]_x - C \equiv C - H \quad (I)$$

wherein:

A with a cycle represents a non-heterocyclic, aromatic, system;

R represents one or more substituent(s), identical or different, being one or more electron-donating group(s) selected from the group consisting of;

linear or branched alkyl groups, linear or branched alkenyl groups, linear or branched halogenoalkyl groups, cycloalkyl groups comprising 3 to 6 carbon atoms, a phenyl group, alkoxy groups of formula $R_5$—O— or thioether groups of formula $R_5$—S—, wherein $R_5$ represents a linear or branched alkyl group comprising 1 to 6 carbon atoms, or a phenyl group, groups of formula —N—$(R_6)_2$, wherein $R_6$ groups, which are identical or different, represent a hydrogen atom, a linear or branched alkyl group comprising 1 to 6 carbon atoms, or a phenyl group, and a —$CF_3$ group $R_1$ and $R_2$, which are identical or different, represent a hydrogen atom, a functional group, a hydrogen group containing 1 to 24 carbon atoms, which is linear or branched, saturated or unsaturated, an acyclic, saturated or unsaturated, aliphatic group, a monocyclic, polycyclic or aromatic cycloaliphatic group, or a line or branched, saturated or unsaturated aliphatic group having a cyclic substituent, $R_3$ and $R_4$ which are identical or different, represent a hydrogen atom or a hydrocarbon group containing 1 to 12 carbon atoms, n is a number smaller than or equal to equal to 5, and x is a number from 1 to 10, with an alkylation agent, which is:

a dialkylsulphate of formula (IVa):

$$R_7\text{—O—SO}_2\text{—O—}R_7 \quad (IVa)$$

wherein $R_7$ represents a linear or branched group containing 1 to 6 carbon atoms, or a halide compound of formula (IVb):

$$R_8\text{—X} \quad (IVb)$$

$R_8$ represents a hydrocarbon group containing 1 to 20 carbon atoms, which is a linear or branched, saturated or unsaturated, acyclic aliphatic group; a saturated, unsaturated or aromatic, monocyclic or polycyclic cycloaliphatic group; or a linear or branched, saturated or unsaturated aliphatic group carrying a cyclic substituent, and X represents a brine, chlorine or iodine atom;

in the presence of an anionisation agent which is an amide base, a metallic alcoholate or an alkali metal, and b) recovering said substituted mixed alkynyl ether of formula (IV):

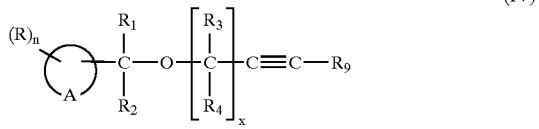

wherein A, R, $R_1$, $R_2$, $R_3$, $R_4$, n and x have the meaning given above, and $R_9$ represents said $R_7$ or $R_8$ group.

2. The process according to claim 1, wherein x is a number from 1 to 5.

3. The process according to claim 1, wherein in formula (1):

$R_1$ and $R_2$, which are identical or different, represent:
a linear or branched saturated or unsaturated acyclic alkyl group, having an hydrocarbon chain, comprising 1 to 6 carbon atoms the hydrocarbon chain being optionally interrupted by a heteroatom, or a functional group, and can optionally substituents,
a linear or branched, saturated or unsaturated, acyclic aliphatic group carrying
a cyclic substituent being optionally substituted, said acyclic group being connected to the cycle via a covalent bond, a heteroatom or a functional group,
a carbocyclic group, saturated or comprising 1 or 2 unsaturated bonds in the cycle, containing 3 to 8 carbon atoms in the cycle, said cycle being optionally substituted,
an aromatic monocyclic carbocyclic group, containing at least 4 carbon atoms in the cycle, said cycle being optionally substituted, or
a $CF_3$ group, for one of groups $R_1$ and $R_2$,
$R_3$ and $R_4$, which are identical or different, represent a hydrogen atom or a hydrocarbon group containing 1 to 12 carbon atoms,
n is a number smaller than or equal to 5, and
x is a number from 1 to 10.

4. The process according to claim 1, wherein in formula (1), A with a cycle is
an aromatic, monocyclic or polycyclic carbocycle.

5. The process according to claim 4, wherein formula (1), A with a cycle is a benzene or naphthalene cycle, optionally substituted.

6. The process according to claim 4, wherein formula (1), A with a cycle carries one or more electron-donating group (s) selected from the group consisting of:
linear or branched alkyl groups, comprising 1 to 4 carbon atoms,
linear or branched alkenyl groups, comprising 2 to 4 carbon atoms,
linear or branched halogenoalkyl groups, comprising 1 to 4 carbon atoms,
a cyclohexyl group,
a phenyl group,
alkoxy groups of formula $R_5$—O— or thioether groups of formula $R_5$—S—, wherein $R_5$ represents a linear or branched alkyl group comprising 1 to 4 carbon atoms, or a phenyl group,
groups of formula —N—$(R_6)_2$, wherein $R_6$ groups, which are identical or different, represent a hydrogen atom, a linear or branched alkyl group comprising 1 to 4 carbon atoms, or a phenyl group, and
a —$CF_3$ group.

7. The process according to claim 1, wherein n is greater than or equal to 2, two groups R and 2 successive atoms on the aromatic cycle being bonded together via an alkylene, alkenylene or alkenylidene group containing 2 to 4 carbon atoms, to form a saturated, unsaturated or aromatic heterocycle containing 5 to 7 carbon atoms, one or more carbon atoms being optionally replaced by a further heteroatom.

8. The process according to claim 1, wherein n is greater than or equal to 2, two groups R and 2 successive atoms on the aromatic cycle being bonded together via an alkylene, alkenylene or alkenylidene group containing 2 to 4 carbon atoms, to form a saturated, unsaturated or aromatic heterocycle containing 5 to 7 carbon atoms, one or more carbon atoms being optionally replaced by a further oxygen atom.

9. The process according to claim 1, wherein $R_3$ and $R_4$, which are identical or different, represent a hydrogen atom or a linear or branched alkyl group containing 1 to 12 carbon atoms.

10. The process according to claim 9, wherein $R_3$ and $R_4$, which are identical or different represent a hydrogen atom or a linear or branched alkyl group containing 1 to 4 carbon atoms.

11. The process according to claim 1, wherein in formula (1):

A with a circle is phenyl,
n is a number equal to or smaller than 4,
x is a number equal to 1, 2 or 3,
R group or groups are electron-donating groups,
$R_1$ and $R_2$ groups, which are identical or different, represent:
a hydrogen atom,
a linear or branched alkyl group containing 1 to 6 carbon atoms,
a cycloalkyl group containing 3 to 8 carbon atoms,
a phenyl group,
a phenylalkyl group containing 7 to 12 carbon atoms, or
a $CF_3$ group, and
$R_3$ and $R_4$ groups, which are identical or different, represent a hydrogen atom or a linear or branched alkyl group containing 1 to 4 carbon atoms.

12. The process according to claim 11, wherein formula (1):
n is 1 or 2,
x is a number equal to 1, 2 or 3,
R group or groups are methylenedioxy or ethylenedioxy groups,
$R_1$ and $R_2$ groups, which are identical or different, represent:
a hydrogen atom,
a methyl, ethyl, propyl, isopropyl, butyl, isobutyl, sec-butyl, tert-butyl group,
a cyclopentyl or cyclohexyl group,
a phenyl group,
a benzyl group, or
a $CF_3$ group, and
$R_3$ ad $R_4$ groups, which are identical o different, represent a hydrogen atom or linear or branched alkyl group containing 1 to 4 carbon atoms.

13. The process according to claim 1, wherein formula (1):
A with a circle is phenyl, n is equal to 1 or 2, R group or groups represent an alkyl or alkoxy group containing 1 to 4 carbon atoms, or a methylenedioxy group, and $R_1$ represents a hydrogen atom or a linear or branched alkyl group containing 1 to 4 carbon atoms.

14. The process according to claim 1, wherein the staring mixed ether is [1-l(prop-1-ynyloxy)ethyl]-3,4 dimethoxybenzene.

15. The process according to claim 1, wherein X represents a chlorine atom or an iodine atom and $R_8$ represents a linear or branched alkyl group containing 1 to 4 carbon atoms.

16. The process according to claim 1, wherein the alkylation agent is dimethylsulphate, methyl iodide, methyl chloride, chloromethane, methyl bromide or bromoethane.

17. The process according to claim 1, wherein the anionisation agent is selected from the group consisting of lithium diisopropylamide, and lithium hexamethyldisilazane.

18. The process according to claim 17, wherein the alkali metal alcoholate is sodium or potassium methylate, ethylate or tert-butylate.

19. The process according to claim 17, wherein the anionisation agent is sodium or potassium amide.

20. The process according to claim 1, wherein the reaction is carried out in an organic solvent that is towards the anionisation agent.

21. The process according to claim 20, wherein the organic solvent is an aliphatic or aromatic hydrocarbon.

22. The process according to claim 1, wherein the temperature of the reaction is comprised between 20° C. and a reflux temperature of the reaction mixture.

23. The process according to claim 22, wherein the temperature is comprised between 50° C. and 80° C.

24. The process according to claim 1, wherein the starting mixed ether of benzyl/alkynyl type of formula (I) and the anionisation agent are brought into contact in a reaction medium, the reaction medium being heated to a desired temperature, the alkylation agent being then added, and the substituted mixed ether of benzyl/alkynyl type obtained being recovered.

* * * * *